United States Patent
Steffens et al.

(10) Patent No.: US 10,940,257 B2
(45) Date of Patent: Mar. 9, 2021

(54) SYSTEMS AND METHODS FOR OXYGENATOR PERFORMANCE EVALUATION

(71) Applicant: Medtronic Vascular, Inc., Santa Rosa, CA (US)

(72) Inventors: Brian Steffens, Maple Grove, MN (US); James Beavers, Houston, TX (US); John Knoll, Brooklyn Park, MN (US); Todd Romine, Big Lake, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 644 days.

(21) Appl. No.: 15/805,896

(22) Filed: Nov. 7, 2017

(65) Prior Publication Data
US 2018/0126057 A1    May 10, 2018

Related U.S. Application Data

(60) Provisional application No. 62/418,832, filed on Nov. 8, 2016.

(51) Int. Cl.
*A61M 1/16*    (2006.01)

(52) U.S. Cl.
CPC ....... *A61M 1/1698* (2013.01); *A61M 2205/18* (2013.01); *A61M 2205/3331* (2013.01);
(Continued)

(58) Field of Classification Search
CPC ............ A61M 1/1698; A61M 2205/18; A61M 2205/3331; A61M 2205/3334; A61M 2205/581; A61M 2205/583; A61M 2205/584; A61M 2205/70; A61M 2205/707

See application file for complete search history.

(56) References Cited

U.S. PATENT DOCUMENTS

| | | |
|---|---|---|
| 8,545,754 B2 | 10/2013 | Carpenter et al. |
| 2008/0171960 A1 | 7/2008 | Brieske et al. |
| (Continued) | | |

FOREIGN PATENT DOCUMENTS

| | | |
|---|---|---|
| EP | 3202436 | 8/2017 |
| EP | 3231461 | 10/2017 |
| (Continued) | | |

OTHER PUBLICATIONS

International Search Report and Written Opinion, PCT/US2017/060476, dated Feb. 13, 2018 (15 pages).

*Primary Examiner* — Benjamin J Klein
(74) *Attorney, Agent, or Firm* — Dicke, Billig & Czaja, PLLC

(57) ABSTRACT

Systems and methods for monitoring oxygenator performance in extracorporeal circuit systems or the like. More particularly, the disclosure relates to systems and methods including a controller programmed to determine oxygenator apparatus flow impedance as a function of an inlet pressure measurement, an outlet pressure measurement and a blood flow rate measurement. The systems and methods may include a communication device that receives signals from the controller to communicate information regarding oxygenator apparatus performance.

18 Claims, 7 Drawing Sheets

(52) U.S. Cl.
   CPC .......... *A61M 2205/3334* (2013.01); *A61M 2205/581* (2013.01); *A61M 2205/583* (2013.01); *A61M 2205/584* (2013.01); *A61M 2205/70* (2013.01); *A61M 2205/707* (2013.01)

(56) References Cited

U.S. PATENT DOCUMENTS

| 2017/0173244 A1* | 6/2017 | Saito | A61M 1/1621 |
| 2017/0258980 A1* | 9/2017 | Katsuki | A61M 1/3666 |

FOREIGN PATENT DOCUMENTS

| JP | 2011045450 | | 3/2011 |
| WO | 2010124087 | A1 | 10/2010 |
| WO | 2016052206 | A1 | 4/2016 |
| WO | 2016092913 | A1 | 6/2016 |

* cited by examiner

SYSTEMS AND METHODS FOR OXYGENATOR PERFORMANCE EVALUATION

CROSS-REFERENCE TO RELATED APPLICATION(S)

The present application claims the benefit of and priority to U.S. provisional patent application Ser. No. 62/418,832 filed Nov. 8, 2016, the disclosure of which is incorporated herein by reference in its entirety.

BACKGROUND

The present disclosure relates to oxygenating blood in an extracorporeal circuit. More particularly, the disclosure relates to systems and methods for evaluating performance of an oxygenator operating in an extracorporeal circuit.

An extracorporeal circuit is commonly used during cardiopulmonary bypass to withdraw blood from the venous portion of the patient's circulation system (via a venous cannula) and return the blood to the arterial portion (via an arterial cannula). The extracorporeal circuit typically includes a venous drainage line, a venous blood reservoir, a blood pump, an oxygenator, a heat exchanger, one or more filters, and blood transporting tubing, ports, and connection pieces interconnecting the components. Oftentimes, an oxygenator and heat exchanger are combined into a single device.

Blood oxygenators are disposable components of extracorporeal circuits and are used to oxygenate blood. In general terms, the oxygenator takes over, either partially or completely, the normal gas exchange function of the patient's lungs. The oxygenator conventionally employs a microporous membrane or bundle comprised of thousands of microporous or semipermeable hollow fibers. Blood flow is directed around the outside surfaces of the hollow fibers. Concurrently, an oxygen-rich gas mixture is passed through the fiber lumens. Due to the relatively high concentration of carbon dioxide in the blood arriving from the patient, carbon dioxide is transferred from the blood, diffusing across the microporous fibers and into the passing stream of oxygenating gas. At the same time, oxygen is transferred from the oxygenating gas, diffusing across the fibers and into the blood. The oxygen content of the blood is thereby raised, and the carbon dioxide content is reduced. After the blood has flowed around the fibers of the oxygenator bundle it must be routed outside the oxygenator housing via a blood outlet port.

One of the most common failure modes of an extracorporeal circuit is when the oxygenator clogs. Extracorporeal life support cases are often conducted with minimal patient heparinization. This can lead to thrombus formation if heparin levels dip below levels that would control thrombus formation. Plugging or clogging of the oxygenator can also occur due to particulate matter or other mechanical issues.

In light of the above, a need exists for improved systems and methods for easy and reliable detection of oxygenator performance impairment.

SUMMARY

Some aspects in accordance with principles of the present disclosure relate to systems and methods for detecting detrimental oxygenator apparatus plugging or impedance in extracorporeal circuit systems or the like. One example oxygenator apparatus establishes a blood flow path from a blood inlet port, through an oxygenator fiber bundle and to a blood outlet port. During use of the oxygenator apparatus, the oxygenator fiber bundle can become clogged, thus reducing the flow of blood through the oxygenator and impairing its performance (i.e. the oxygenator's ability to oxygenate a sufficient amount of blood). Aspects of the disclosure provide systems and methods for measuring and monitoring oxygenator apparatus impedance to identify the progression of thrombus formation or other blockages in the oxygenator apparatus.

One example system includes an oxygenator apparatus having a first sensor for generating an inlet pressure measurement, a second for generating an outlet pressure measurement and a third sensor for generating a blood flow rate measurement. The inlet pressure measurement, outlet pressure measurement and blood flow rate measurement are used to calculate flow impedance and the systems disclosed herein communicate information relating to the same.

One method of monitoring oxygenator apparatus performance begins with fluidly connecting the blood inlet and outlet ports of the oxygenator apparatus into an extracorporeal circuit. Blood from the patient is delivered to the blood inlet port and is oxygenated when passing through the oxygenator fiber bundle. Blood flow impedance is calculated by a controller, as a function of a measured pressure differential divided by blood flow rate. In some embodiments, a baseline impedance is established. Blood from the patient is continually passed through the oxygenator apparatus and impedance measurements are repeatedly monitored to determine operational impedance. In situations where the difference between the baseline impedance and the operational impedance exceeds a predetermined threshold, an alert is communicated to the caregiver or clinician via a communication device to notify the caregiver that the oxygenator apparatus performance is impaired to the extent that the oxygenator apparatus should be replaced or heparin dosage should be reconsidered. In some disclosed systems and methods, the controller and communication device are provided by a standalone oxygenator apparatus used in a perfusion circuit and in other embodiments, systems and methods provide the controller and communication device apart from the oxygenator apparatus as provided to a user. With the disclosed methods, oxygenator apparatus impairment determinations are relatively effortless and oxygenator apparatus performance can be monitored by one having little training or experience.

DETAILED DESCRIPTION

Figure 1:
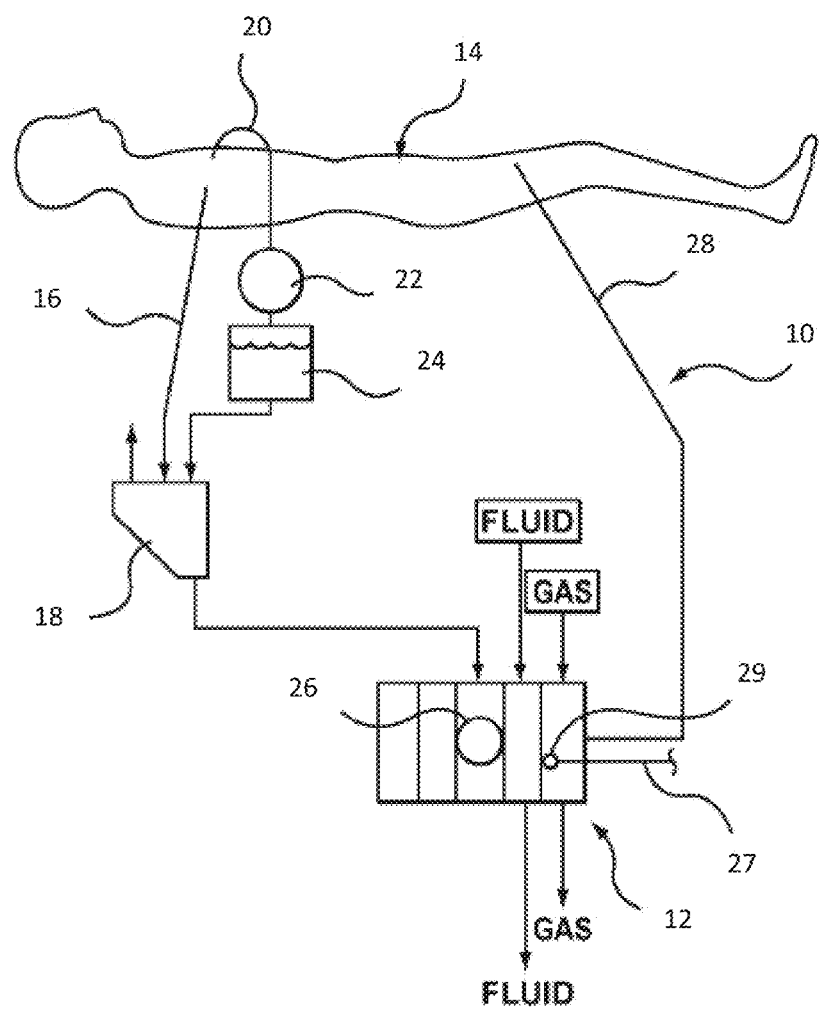
FIG. 1 is a schematic drawing of an extracorporeal circuit including an oxygenator apparatus for oxygenating patient blood.

FIG. 1 schematically illustrates an exemplary extracorporeal circuit 10 that can be modified and used in accordance with the teachings of the present disclosure. The extracorporeal circuit 10 is a system or device in which blood is desired to be oxygenated (and, optionally, temperature controlled). One particular system is an electromechanical extracorporeal circulatory support system known as a cardiopulmonary bypass (CPB) system, commercially sold by Medtronic, Inc., of Minneapolis, Minn. under the trade name Performer-CPB System. Other systems are contemplated by the present disclosure. The exemplary extracorporeal circuit 10 includes an oxygenator apparatus 12 and generally draws blood of a patient 14 during cardiovascular surgery through a venous line 16. Venous blood drawn from the patient 14 is discharged into a venous reservoir 18. Cardiotomy blood and surgical field debris are aspirated by a suction device 20 and are pumped by a pump 22 into a cardiotomy reservoir 24. Once de-foamed and filtered, the cardiotomy blood is also discharged into the venous reservoir 18. Alternatively, the function of the cardiotomy reservoir 24 may be integrated into the venous reservoir 18. In the venous reservoir 18, air entrapped in the venous blood rises to the surface of the blood and is vented to the atmosphere.

A pump 26 draws blood from the venous reservoir 18 and pumps it through the oxygenator apparatus 12. Some exemplary types of pumps 26 include, but are not limited to, roller pumps and centrifugal pumps. The pump 26 may be external to the oxygenator apparatus 12 as shown, or may alternatively be incorporated into the oxygenator apparatus 12. As described above, the blood is de-aerated, optionally temperature controlled, and oxygenated by the oxygenator apparatus 12, and then returned to the patient 14 via an arterial line 28.

In one example embodiment, during operation of the oxygenator apparatus 12 as part of the circuit 10, air is purged from oxygenator apparatus 12 via an air purge port 27 (referenced generally in FIG. 1). In some embodiments, during normal operation this purge will consist solely of blood, which may detract from the total blood flow out of the oxygenator apparatus 12. When air enters the oxygenator apparatus 12, the inlet geometry forces the air out of the air purge port 27 and through an air purge line 29.

One of the most common failure modes of an extracorporeal circuit is when a patient on extracorporeal life support or extracorporeal membrane oxygenation therapy is when the oxygenator apparatus 12 clogs. Extracorporeal life support cases are often conducted with minimal patient heparinization. This can lead to thrombus formation if heparin levels dip below levels that would control thrombus formation. Clogging of the oxygenator apparatus 12 can also occur due to particulate matter or other mechanical issues. Therefore, the present disclosure further includes methods of monitoring oxygenator apparatus performance and alerting a caregiver when the oxygenator performance is nearing an unacceptable threshold and/or when it is recommended that the oxygenator apparatus be replaced or patient heparin dosage can be revised to address thrombus formation. Further embodiments can include providing various stages of alert (e.g., green, yellow, red) for when the oxygenator is adequately performing (green), when the oxygenator apparatus is nearing inadequate performance (yellow) and when the oxygenator apparatus is insufficiently performing (red). The methods and systems disclosed herein make oxygenator apparatus monitoring and maintenance effortless and can be performed by one having little training or experience.

Figure 2:
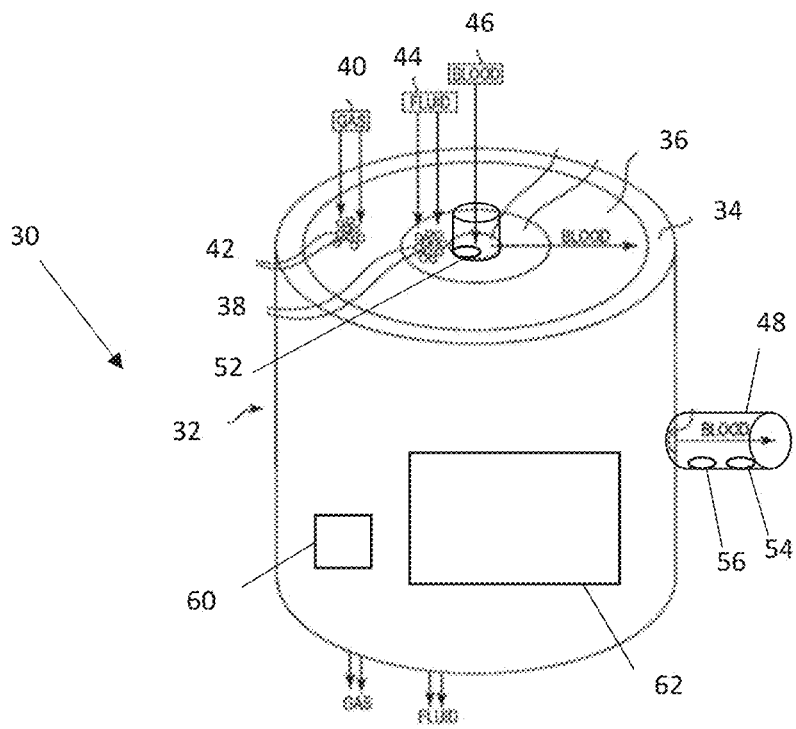
FIG. 2 is a schematic drawing of an example oxygenator apparatus showing blood, fluid medium and gas medium flow through the oxygenator apparatus.
Figure 3:
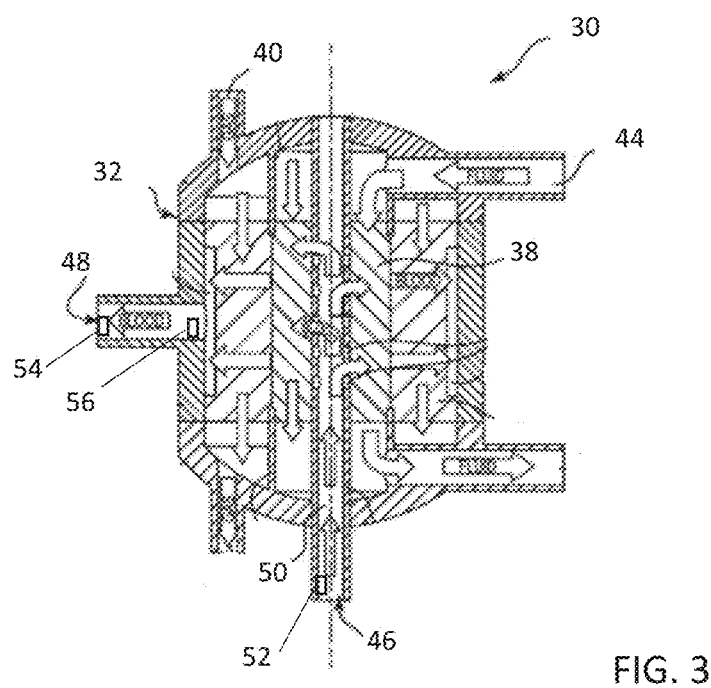
FIG. 3 is a cross-sectional, side view of the oxygenator apparatus schematically shown in FIG. 2.

Components of one system 30, including a non-limiting example of an oxygenator apparatus 32 useful for treating blood in an extracorporeal circuit, are shown in FIGS. 2-3. In general terms, the oxygenator apparatus 32 includes a housing 34 and an oxygenator 36. The oxygenator 36 includes a plurality of gas exchange elements (referenced generally as oxygenator fiber bundle 38) that can be connected to a gas supply 40. To effectuate temperature control of the blood, the oxygenator apparatus 32 can optionally include a heat exchanger 42 (a plurality of heat exchange elements are referenced generally) for connection to a fluid supply 44. The housing 34 provides or maintains a blood inlet port 46 and a blood outlet port 48. A blood flow path 50 is defined from the blood inlet port 46 to the blood outlet port 48, with blood oxygenation occurring as the blood interfaces with an oxygenator fiber bundle 38. Additionally disclosure regarding the example oxygenator 36 and heat exchanger 42 are provided in U.S. Pat. No. 8,545,754 (Carpenter et al.), the disclosure of which is hereby incorporated by reference in its entirety.

The system 30 further includes a first sensor 52 proximate the blood inlet port 46 for generating an inlet pressure measurement and a second sensor 54 proximate the blood outlet port 48 for generating an outlet pressure measurement. The system 30 further includes a third sensor 56 for generating a blood flow rate measurement. In various embodiments, the third sensor 56 is proximate the blood outlet port 48 or downstream of the blood outlet port 48 (see also, FIG. 1). The disclosure is not intended to be limited to any specific placement of the first, second and third sensors 52, 54, 56. Any placement of the first-third sensors 52, 54, 56 capable of determining a pressure differential and blood flow rate measurement are acceptable.

In this embodiment, the housing 34 further carries a controller 60 and/or communication device 62. The controller 60 is electronically connected with the first, second and third sensors 52, 54, 56 as well as the communication device 62. The controller 60 is programmed to determine flow impedance through the oxygenator fiber bundle 38 as a function of the inlet pressure measurement, the outlet pressure measurement and the blood flow rate measurement generated by the first, second and third sensors 52, 54, 56. The controller 60 is further configured to prompt the communication device 62 to communicate information indicative of the determined oxygenator apparatus 32 performance, including, but not limited to blood flow impedance. In one embodiment, the blood flow impedance is defined as:

$$\text{(inlet pressure measurement} - \text{outlet pressure measurement)/blood flow rate measurement} \qquad (1)$$

Figure 4:
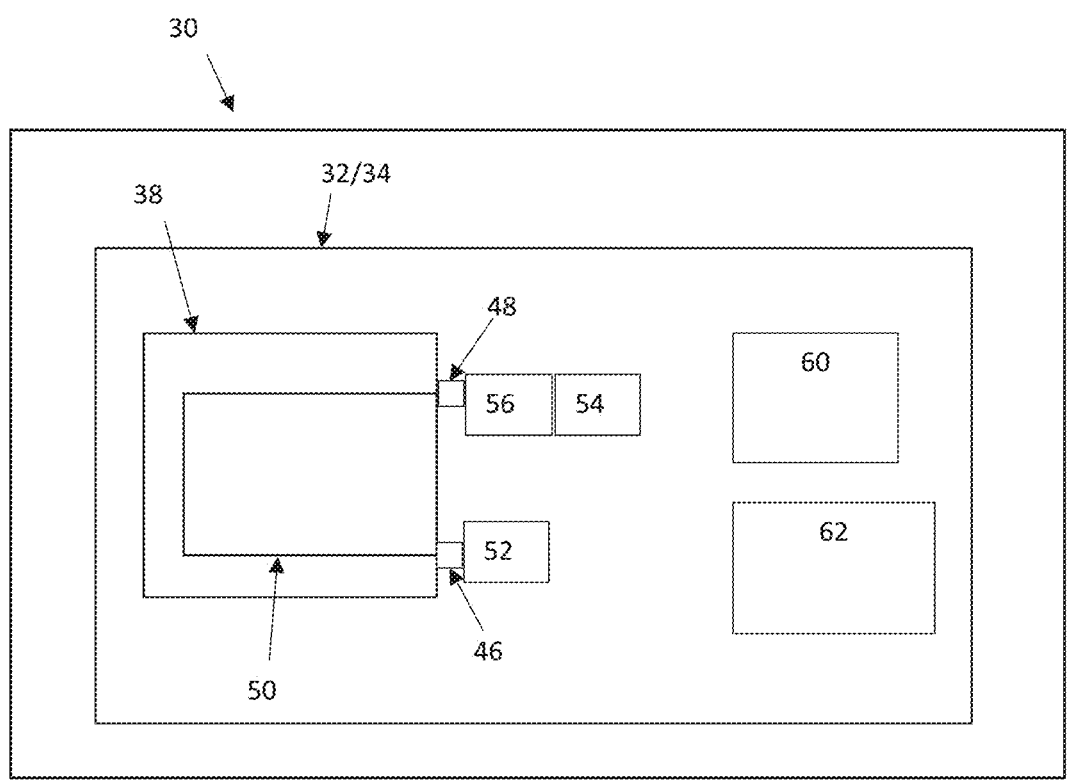
FIG. 4 is a schematic diagram of one system for monitoring impairment of an oxygenator apparatus, such as the oxygenator apparatus of FIGS. 2-3.

With the above in mind, FIG. 4 schematically illustrates the system 30 of FIGS. 2-3 for oxygenating blood in an extracorporeal circuit (e.g., circuit 10 of FIG. 1). As previously indicated, the system 30 includes the oxygenator apparatus 32 having the housing 34 carrying the oxygenator 36 as well as the communication device 62 (e.g., display and/or speaker) and controller 60. Alternatively, the controller 60 and communication device 62 can be provided elsewhere in the system 30, separate from the housing 34.

Figure 5:
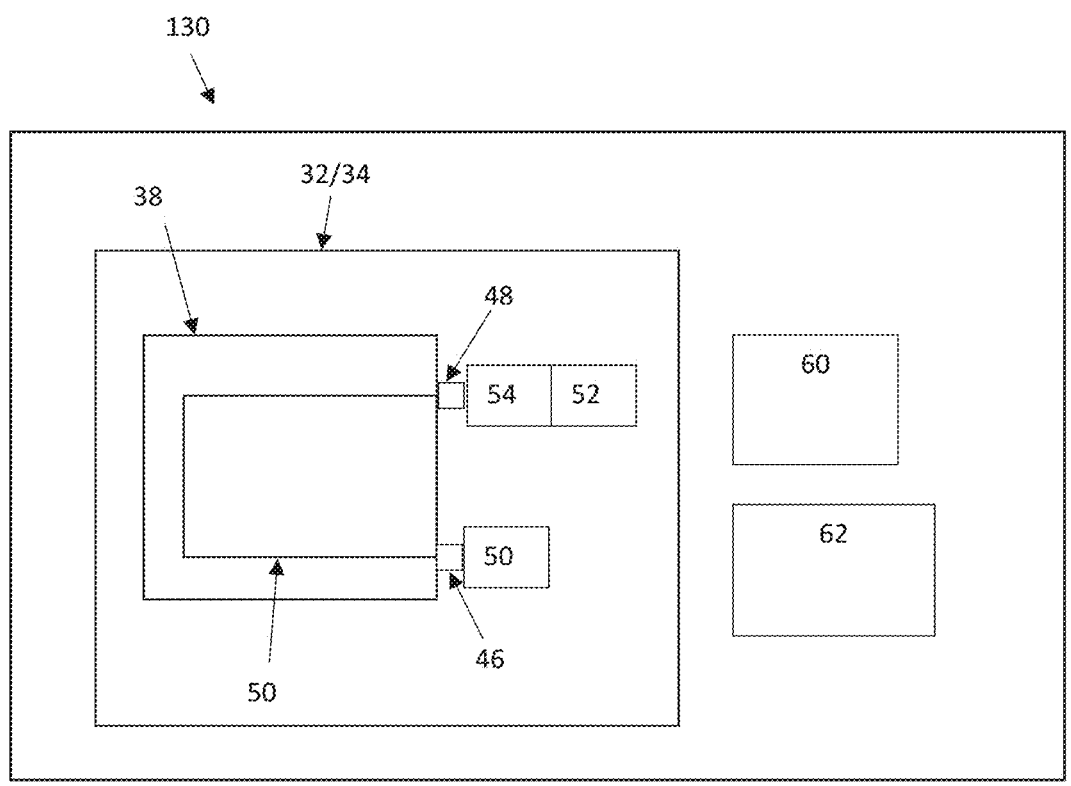
FIG. 5 is a schematic diagram of an alternate system, similar to that of FIG. 4.

FIG. 5 schematically illustrates one such alternate system 130. The system 130 differs from system 30 only in that the controller 60 and communication device 62 are not part of or carried by the housing 34. In this embodiment, the controller 60 and communication device 62 are provided as separate parts of the system 130. As indicated with reference numerals, it will be understood that all other aspects of the system 130 are configured and operate in ways previously disclosed with respect to system 30.

Figure 6:
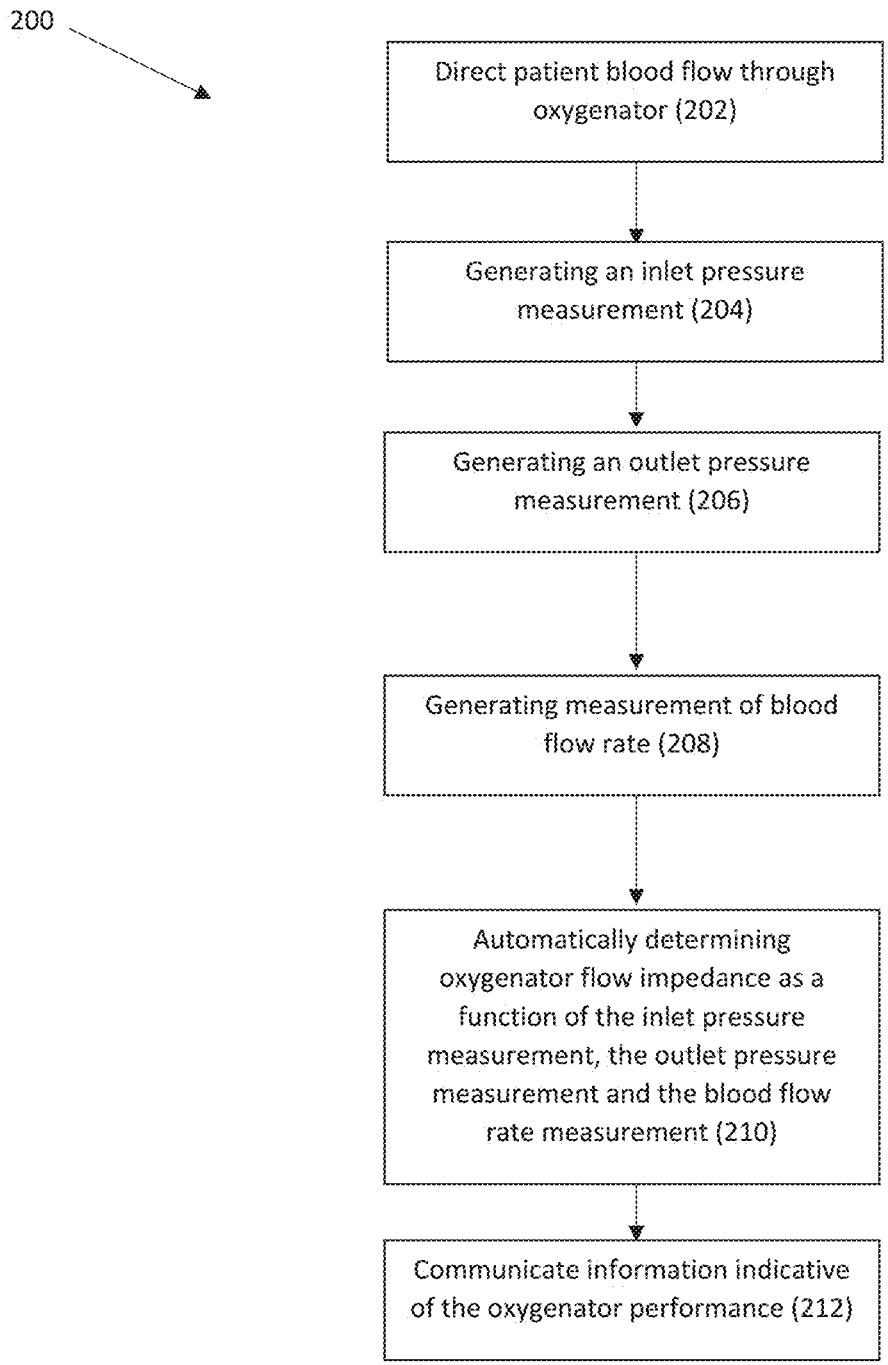
FIG. 6 is a flow chart generally illustrating one method of communicating information indicative of oxygenator apparatus performance.

Referring also to FIG. 6, one example method for automatically characterizing the performance of the oxygenator apparatus 100 includes directing patient blood flow through an oxygenator apparatus 102, generating an inlet pressure measurement 104, generating an outlet pressure measurement 106 and also sensing a blood flow rate measurement 108. In certain embodiments, the inlet pressure measurement is generated at or adjacent the blood inlet port 46, the outlet pressure measurement is generated proximate the blood outlet port 48 and the flow rate is generated proximate the blood outlet port 48 (as shown in FIGS. 2-5). The method further comprises utilizing the controller 60 to automatically determine oxygenator apparatus 32 flow impedance as a function of the inlet pressure measurement, the outlet pressure measurement and blood flow rate measurement 110 to determine and communicate information indicative of the oxygenator apparatus flow impedance to a clinician. For example, Equation (1) is applied via the controller 60 and then the controller 60 sends a signal to the communication device 62 to communicate data 112 (e.g., via display and/or audio) regarding either oxygenator apparatus flow impedance and/or the measurements obtained in steps 104 through 108.

In various embodiments, the controller 60 is further programmed to determine a baseline oxygenator apparatus 32 flow impedance at a first point in time and a second point in time, after the first point in time, and then also prompt the communication device 62 to communicate information indicative of a comparison between the baseline oxygenator apparatus flow impedance and the current oxygenator apparatus flow impedance. In even further embodiments, the controller 60 can be programmed to generate oxygenator apparatus flow impedance trending information based on a multiplicity of sequentially determined oxygenator apparatus flow impedances; and determine an end-of-life criteria for the oxygenator apparatus based upon the oxygenator apparatus flow impedance trending information. Alternatively, or in addition, the controller 60 can be programmed to prompt the communication device 62 to communicate an alert when the determined difference exceeds a predetermined value. In yet further embodiments, when significant impedance is identified, patient heparin dosage can be revised, which may reduce impedance due to blood clotting without the need for replacing the oxygenator apparatus. Further embodiments can include providing various stages of alert (e.g., green, yellow, red) for when the oxygenator is adequately performing (green), when the oxygenator apparatus is nearing inadequate performance (yellow) and when the oxygenator apparatus is insufficiently performing (red). Such a "yellow" stage of alert can also include a prediction when the oxygenator will transition to a "red" state of alert (i.e. when the oxygenator will need to be replaced). This would allow a nurse who notices rising oxygenator impedance the knowledge that they have time to allow specialists (perfusionists) to be available, potentially after one or more shifts. The nurse would be informed that the oxygenator is starting to clot, but it is not critical yet and can wait until other staffing is available. In one example, the green stage is when the transmembrane pressure range is between 150 mmHg-250 mmHg, the yellow stage is greater than 250 mmHg-350 mmHg and the red stage is when the transmembrane pressure range exceeds 350 mmHg. Such various stages of alert can be visual, audial or the like.

Figure 7:
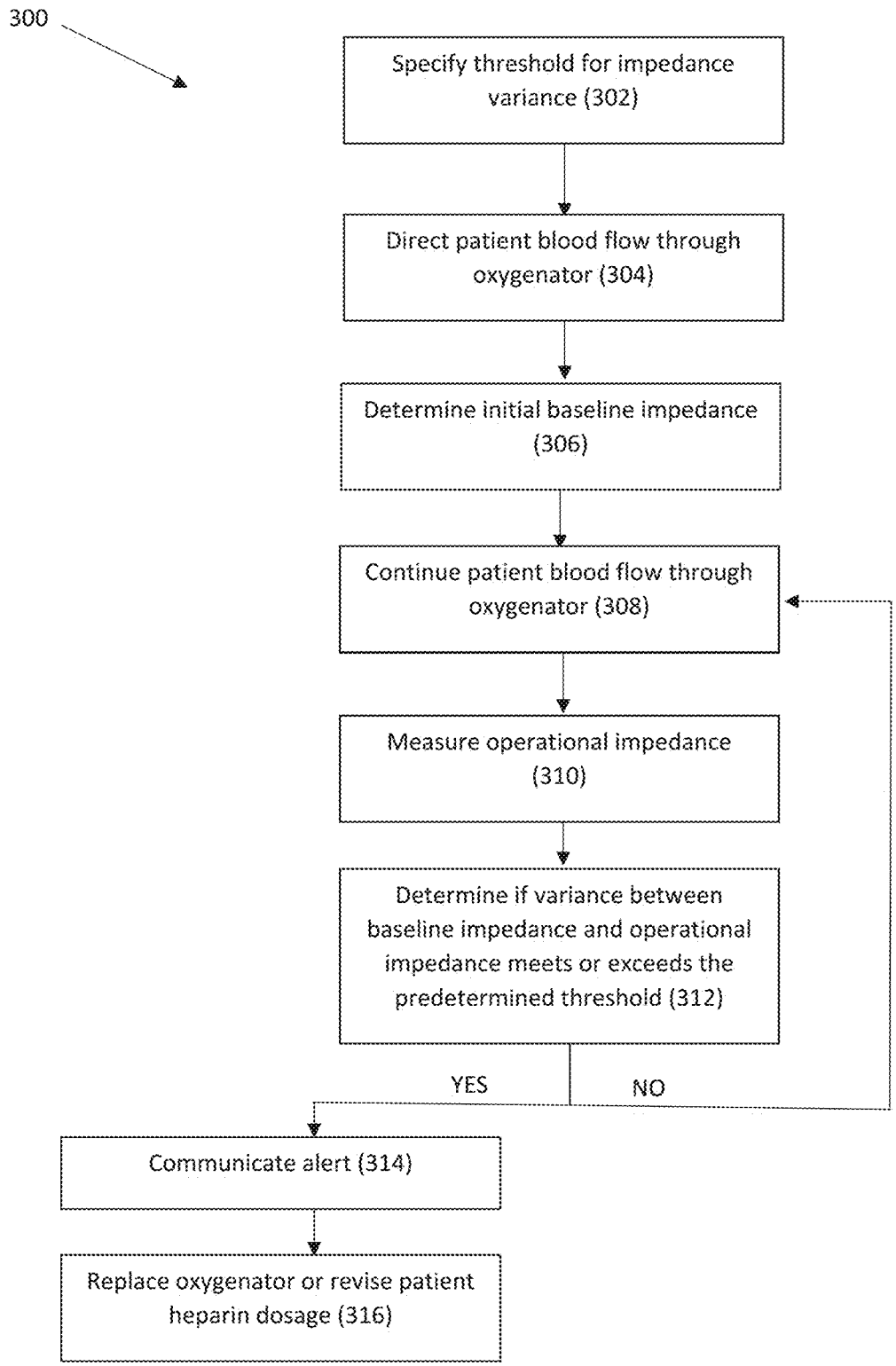
FIG. 7 is a flow chart generally illustrating one example method of detecting oxygenator apparatus impairment.

Reference is now also made to FIG. 7, which illustrates one such method of monitoring oxygenator apparatus performance 200. The method can begin with providing an oxygenator apparatus incorporated into a system for oxygenating blood, such as the extracorporeal circuit 10 disclosed above. Before venous blood is drawn from the patient, a threshold variance establishing blood impedance within the oxygenator apparatus 32 is established 202. This threshold can be established by the oxygenator apparatus manufacturer or, alternatively, selected or adjusted by the user. After the predetermined threshold is established 202, venous blood is drawn from the patient and ultimately directed into the oxygenator apparatus 204 via the blood inlet port 46. From the blood inlet port 46, the venous blood is oxygenated, optionally heated via the heat exchanger 42, and discharged out of the oxygenator apparatus 32 via the blood outlet port 48. First, second and third sensors 52, 54, 56 are positioned to measure the blood flow rate and pressure differential across the oxygenator apparatus 32. From this information, a normalized or baseline impedance is calculated 206:

Impedance=(inlet pressure measurement−outlet pressure measurement)/blood flow rate measurement As will be understood, the baseline impedance can vary greatly on a number of factors particular to the electromechanical extracorporeal circulatory support system, blood characteristic, etc. After the baseline impedance is determined 206, venous blood flow through the oxygenator apparatus 32 continues 208 and operational impedance is repeatedly measured 210. With at least some of the operational impedance measurements, the operational impedance measurements are compared to the baseline impedance measurement via the controller 60 to determine if a variance, if any, between the baseline impedance and the operational impedance measurement meets or exceeds the predetermined threshold 212. If the threshold variance is not met, operation of the oxygenator apparatus 32 continues and venous blood continues to flow through the oxygenator apparatus 208. If the threshold variance is met and/or exceeded, an alert or communication 214 is provided (e.g., via communication device 62) to the clinician that oxygenator apparatus 32 performance is impaired to the extent that the oxygenator apparatus should be replaced or heparin dosage should be revised 216 to maintain adequate oxygenator apparatus performance. The alert can be a visual, audial or both, for example.

Example A

Figure 8A:
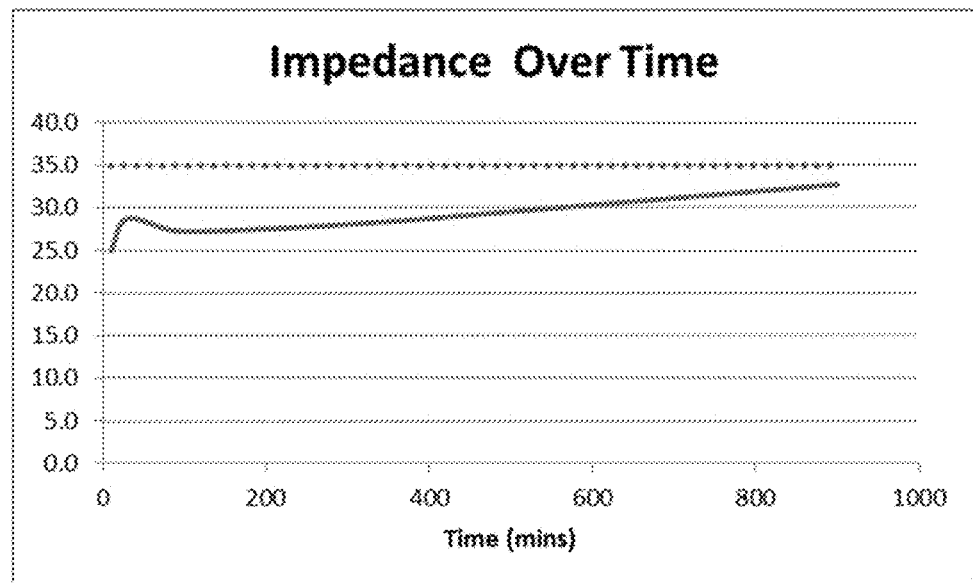
FIG. 8A is a graph illustrating a first example of impedance trending information.

FIG. 8A a graph illustrating generated impedance values of an oxygenator apparatus (i.e. generated impedance trending information). Such impedance trending information can be used by the controller to monitor oxygenator performance. In Example A, the oxygenator apparatus flow impedance trending information is generated based on a multiplicity of sequentially determined oxygenator apparatus flow impedances in accordance with Equation (1). The data generated in this Example is provided in Table 1. In this Example, the predetermined threshold variance is 35 mmHG*min/L. Therefore, should the calculated impedance exceed 35 mmHG*min/L, the controller is configured to prompt the communication device to provide an alert, as discussed above. In the present Example, throughout the test period the oxygenator apparatus is sufficiently operational and the measured oxygenator apparatus impedance does not reach a value great enough to trigger an alert.

TABLE 1

| Time (mins) | Inlet pressure measurement (mmHG) | Outlet pressure measurement (mmHG) | Inlet pressure − outlet pressure | Blood Flow Rate (L/min) | Impedance (mmHG * min/L) | Predetermined Threshold of Impedance (mmHG * min/L) |
|---|---|---|---|---|---|---|
| 10 | 337 | 163 | 174 | 7 | 24.9 | 35 |
| 30 | 368 | 167 | 201 | 7 | 28.7 | 35 |
| 90 | 358 | 167 | 191 | 7 | 27.3 | 35 |
| 180 | 361 | 169 | 192 | 7 | 27.4 | 35 |
| 270 | 362 | 167 | 195 | 7 | 27.9 | 35 |
| 360 | 367 | 168 | 199 | 7 | 28.4 | 35 |
| 450 | 372 | 168 | 204 | 7 | 29.1 | 35 |
| 540 | 377 | 168 | 209 | 7 | 29.9 | 35 |
| 630 | 382 | 168 | 214 | 7 | 30.6 | 35 |
| 720 | 387 | 168 | 219 | 7 | 31.3 | 35 |
| 810 | 392 | 168 | 224 | 7 | 32.0 | 35 |
| 900 | 397 | 168 | 229 | 7 | 32.7 | 35 |

Example B

Figure 8B:
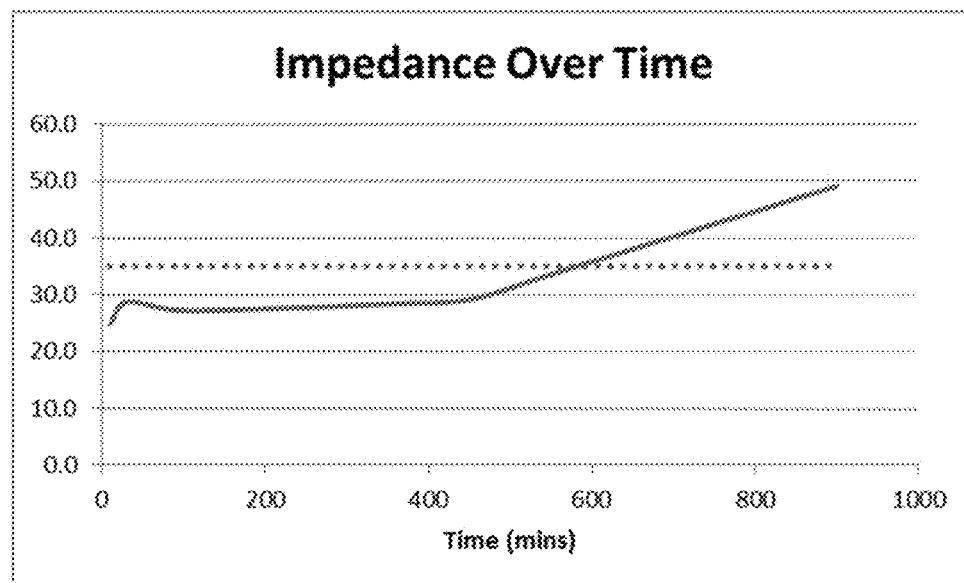
FIG. 8B is a graph illustrating a second example of impedance trending information.

FIG. 8B graph illustrating a second example showing impedance values of an oxygenator apparatus (i.e. generated impedance trending information). In Example B, the oxygenator apparatus flow impedance trending information is generated based on a multiplicity of sequentially determined oxygenator apparatus flow impedances in accordance with Equation (1). The data generated in this Example is provided in Table 2 below. In this Example, the predetermined threshold for impedance is also set at 35 mmHG*min/L. In the present Example, the oxygenator apparatus performance is sufficiently compromised at minute 630 when the generated impedance reaches 37.1 mmHG*min/L. In this Example, the controller would prompt the communication device to provide an alert indicative of the inadequate oxygenator apparatus performance due to blood flow impedance at minute 630.

TABLE 2

| Time (mins) | Inlet pressure measurement (mmHG) | Outlet pressure measurement (mmHG) | Inlet pressure − outlet pressure | Blood Flow Rate (L/min) | Impedance (mmHG * min/L) | Predetermined Threshold of Impedance (mmHG * min/L) |
|---|---|---|---|---|---|---|
| 10 | 337 | 163 | 174 | 7 | 24.9 | 35 |
| 30 | 368 | 167 | 201 | 7 | 28.7 | 35 |
| 90 | 358 | 167 | 191 | 7 | 27.3 | 35 |
| 180 | 361 | 169 | 192 | 7 | 27.4 | 35 |
| 270 | 362 | 167 | 195 | 7 | 27.9 | 35 |
| 360 | 367 | 168 | 199 | 7 | 28.4 | 35 |
| 450 | 372 | 168 | 204 | 7 | 29.1 | 35 |
| 540 | 400 | 168 | 232 | 7 | 33.1 | 35 |
| 630 | 428 | 168 | 260 | 7 | 37.1 | 35 |
| 720 | 456 | 168 | 288 | 7 | 41.1 | 35 |
| 810 | 484 | 168 | 316 | 7 | 45.1 | 35 |
| 900 | 512 | 168 | 344 | 7 | 49.1 | 35 |

Examples A and B are hypothetical scenarios and do not represent actual test data.

Although the present disclosure has been described with reference to preferred embodiments, workers skilled in the art will recognize that changes can be made in form and detail without departing from the spirit and scope of the present disclosure.

What is claimed is:

1. A system for oxygenating blood in an extracorporeal circuit, the system comprising:

an oxygenator apparatus including:
    a housing defining a blood inlet port, a blood outlet port and a blood flow path from the blood inlet port to the blood outlet port, and
    a fiber bundle disposed within the housing and including a plurality of gas exchange elements;
a first sensor proximate the blood inlet port for generating an inlet pressure measurement;
a second sensor proximate the blood outlet port for generating an outlet pressure measurement;
a third sensor for generating a blood flow rate measurement;
a communication device; and
a controller electronically connected to the first, second and third sensors and the communication device, the controller programmed to:
    determine oxygenator apparatus flow impedance as a function of the inlet pressure measurement, the outlet pressure measurement and the blood flow rate measurement,
    determine a baseline oxygenator apparatus flow impedance at a first point in time,
    determine a current oxygenator apparatus flow impedance at a second point in time, the second point in time being after the first point in time, and
    prompt the communication device to communicate information indicative of the determined oxygenator apparatus flow impedance including a comparison between the baseline oxygenator apparatus flow impedance and the current oxygenator flow apparatus impedance.

2. The system of claim 1, wherein the controller is programmed to determine oxygenator apparatus flow impedance as:

(inlet pressure measurement−outlet pressure measurement)/blood flow rate measurement.

3. The system of claim 1, wherein the communication device and the controller are carried by the housing.

4. The system of claim 1, wherein the communication device and the controller are separate from the housing.

5. The system of claim 1, wherein at least one of the first, second and third sensors are carried by the housing.

6. The system of claim 1, wherein at least one of the first, second and third sensors are not attached to the housing.

7. The system of claim 1, wherein the communication device provides a communication selected from the group consisting of a visual communication and an audible communication.

8. The system of claim 1, wherein the third sensor is proximate the blood outlet port.

9. A system for oxygenating blood in an extracorporeal circuit, the system comprising:
    an oxygenator apparatus including:
        a housing defining a blood inlet port, a blood outlet port and a blood flow path from the blood inlet port to the blood outlet port, and
        a fiber bundle disposed within the housing and including a plurality of gas exchange elements;
    a first sensor proximate the blood inlet port for generating an inlet pressure measurement;
    a second sensor proximate the blood outlet port for generating an outlet pressure measurement;
    a third sensor for generating a blood flow rate measurement;
    a communication device; and
    a controller electronically connected to the first, second and third sensors and the communication device, the controller programmed to:
        determine oxygenator apparatus flow impedance as a function of the inlet pressure measurement, the outlet pressure measurement and the blood flow rate measurement,
        determine a first oxygenator apparatus flow impedance at a first point in time,
        determine a second oxygenator flow apparatus impedance at a second point in time, the second point in time being after the first point in time,
        determine a difference between the first and second oxygenator apparatus flow impedances, and
        prompt the communication device to communicate information indicative of the determined oxygenator apparatus flow impedance including prompt the communication device to communicate an alert when the determined difference exceeds a predetermined value.

10. A system for oxygenating blood in an extracorporeal circuit, the system comprising:
    an oxygenator apparatus including:
        a housing defining a blood inlet port, a blood outlet port and a blood flow path from the blood inlet port to the blood outlet port, and
        a fiber bundle disposed within the housing and including a plurality of gas exchange elements;
    a first sensor proximate the blood inlet port for generating an inlet pressure measurement;
    a second sensor proximate the blood outlet port for generating an outlet pressure measurement;
    a third sensor for generating a blood flow rate measurement;
    a communication device; and
    a controller electronically connected to the first, second and third sensors and the communication device, the controller programmed to:
        determine oxygenator apparatus flow impedance as a function of the inlet pressure measurement, the outlet pressure measurement and the blood flow rate measurement,
        prompt the communication device to communicate information indicative of the determined oxygenator apparatus flow impedance,
        generate oxygenator apparatus flow impedance trending information based on a multiplicity of sequentially determined oxygenator apparatus flow impedances, and
        determine an end-of-life criteria for the oxygenator apparatus based upon the oxygenator apparatus flow impedance trending information.

11. An oxygenator apparatus for oxygenating blood in an extracorporeal circuit, the oxygenator apparatus comprising:
    a housing defining a blood inlet port, a blood outlet port and a flow path from the blood inlet port to the blood outlet port;
    a fiber bundle disposed within the housing and including a plurality of gas exchange elements;
    a first sensor carried by the housing for sensing an inlet pressure measurement proximate the blood inlet port;
    a second sensor carried by the housing for sensing a outlet pressure measurement proximate the blood outlet port;
    a third sensor for generating a blood flow rate measurement;
    a communication device; and
    a controller electronically connected to the first, second and third sensors and the communication device, the controller programmed to:
        determine oxygenator apparatus flow impedance as a function of the inlet pressure measurement, the outlet pressure measurement and the blood flow rate measurement,
        determine a baseline oxygenator apparatus flow impedance at a first point in time,
        determine a current oxygenator apparatus flow impedance at a second point in time, the second point in time being after the first point in time, and
        prompt the communication device to communicate information indicative of the determined oxygenator apparatus flow impedance including prompt the communication device to communicate information indicative of a comparison between the baseline oxygenator apparatus flow impedance and the current oxygenator apparatus flow impedance.

12. The apparatus of claim 11, wherein the communication device provides a communication selected from the group consisting of a visual communication and an audible communication.

13. The apparatus of claim 11, wherein the third sensor is proximate the blood outlet port.

14. The apparatus of claim 11, wherein the controller is programmed to determine oxygenator apparatus flow impedance as:

(inlet pressure measurement−outlet pressure measurement)/blood flow rate measurement.

15. An oxygenator apparatus for oxygenating blood in an extracorporeal circuit, the oxygenator apparatus comprising:
- a housing defining a blood inlet port, a blood outlet port and a flow path from the blood inlet port to the blood outlet port;
- a fiber bundle disposed within the housing and including a plurality of gas exchange elements;
- a first sensor carried by the housing for sensing an inlet pressure measurement proximate the blood inlet port;
- a second sensor carried by the housing for sensing a outlet pressure measurement proximate the blood outlet port;
- a third sensor for generating a blood flow rate measurement;
- a communication device; and
- a controller electronically connected to the first, second and third sensors and the communication device, the controller programmed to:
  - determine oxygenator apparatus flow impedance as a function of the inlet pressure measurement, the outlet pressure measurement and the blood flow rate measurement,
  - determine a first oxygenator apparatus flow impedance at a first point in time,
  - determine a second oxygenator apparatus flow impedance at a second point in time, the second point in time being after the first point in time,
  - determine a difference between the first and second oxygenator apparatus flow impedances, and
  - prompt the communication device to communicate information indicative of the determined oxygenator apparatus flow impedance including prompt the communication device to communicate a warning when the determined difference exceeds a predetermined value.

16. An oxygenator apparatus for oxygenating blood in an extracorporeal circuit, the oxygenator apparatus comprising:
- a housing defining a blood inlet port, a blood outlet port and a flow path from the blood inlet port to the blood outlet port;
- a fiber bundle disposed within the housing and including a plurality of gas exchange elements;
- a first sensor carried by the housing for sensing an inlet pressure measurement proximate the blood inlet port;
- a second sensor carried by the housing for sensing a outlet pressure measurement proximate the blood outlet port;
- a third sensor for generating a blood flow rate measurement a communication device; and
- a controller electronically connected to the first, second and third sensors and the communication device, the controller programmed to:
  - determine oxygenator apparatus flow impedance as a function of the inlet pressure measurement, the outlet pressure measurement and the blood flow rate measurement,
  - prompt the communication device to communicate information indicative of the determined oxygenator apparatus flow impedance,
  - generate oxygenator apparatus flow impedance trending information based on a multiplicity of sequentially determined oxygenator apparatus flow impedances, and
  - determine an end-of-life criteria for the oxygenator apparatus based upon the oxygenator apparatus flow impedance trending information.

17. A method for maintaining oxygenating performance of an extracorporeal circuit, the extracorporeal circuit including an oxygenator apparatus including a housing and a fiber bundle having a plurality of gas exchange elements, the housing defining a blood flow path between a blood inlet port and a blood outlet port, the fiber bundle disposed within the housing, the method comprising:
- determining a first oxygenator apparatus flow impedance at a first point in time;
- determining a second oxygenator apparatus flow impedance at a second point in time, the second point in time being after the first point in time; and
- comparing the first oxygenator apparatus flow impedance and the second oxygenator apparatus flow impedance; and
- communicate information to a clinician indicative of the oxygenator apparatus flow impedance.

18. The method of claim 17, wherein the oxygenator apparatus flow impedance is determined as:

(inlet pressure measurement−outlet pressure measurement)/blood flow rate measurement.

* * * * *